United States Patent

Price et al.

[11] Patent Number: 6,114,849
[45] Date of Patent: Sep. 5, 2000

[54] FLEXIBLE EDDY CURRENT TEST PROBE

[75] Inventors: Larry Stephen Price; David Justin Watson, both of Richland, Wash.

[73] Assignee: United Western Technologies Corp., Pasco, Wash.

[21] Appl. No.: 09/062,390

[22] Filed: Apr. 17, 1998

[51] Int. Cl.$^7$ .................................................. G01N 27/90
[52] U.S. Cl. ........................ 324/240; 324/219; 336/200
[58] Field of Search ................................... 324/219–221, 324/228, 234, 236–238, 239–243, 260–262; 336/200–208, 232, 233, 234

[56] References Cited

U.S. PATENT DOCUMENTS

| | | | |
|---|---|---|---|
| 4,675,605 | 6/1987 | Watjen | 324/228 |
| 4,881,031 | 11/1989 | Pfisterer et al. | 324/242 |
| 5,389,876 | 2/1995 | Hedengren et al. | 324/233 |
| 5,600,240 | 2/1997 | Mikhailovich et al. | 324/219 |
| 5,623,204 | 4/1997 | Wilkerson | 324/240 |

*Primary Examiner*—Jay Patidar
*Attorney, Agent, or Firm*—Marger Johnson & McCollom

[57] ABSTRACT

An eddy current test probe having a flexible sensor assembly for non-destructive testing of conductive parts. The flexible eddy current sensor assembly includes a coil assembly having a drive coil and a receive coil positioned in close proximity to each other to maximize inductive coupling. The drive coil receives an alternating voltage from an alternating voltage source. The receive coil is coupled to a visual display which displays the eddy current signal strength in appropriate units. The coil assembly is formed on a flexible membrane. The flexible membrane allows the coil assembly to contour to the PUT surface. By doing so, surface coupling is not only maintained but maximized between the PUT and the coil assembly which, in turn, improves the induced electromagnetic field. A wear resistant film is formed around the outside of the compliance membrane enclosing the coil assembly. The wear resistant film prevents damage to the coils from the inevitable surface irregularities and abrasive particles found in PUTs. The flexible membrane is layered on a flexible compliance membrane. The compliance membrane provides a degree of stiffness to the flexible membrane for maintaining close surface coupling with the PUT. An electromagnetic shield is optionally formed on the flexible membrane on each side of the coil assembly and underneath the wear resistant film. The electromagnetic shield contains the energy exchange between the PUT and the coil assembly by preventing the electromagnetic field induced in the PUT from spreading out on the PUT. The electromagnetic shield is of particular importance when the sensor assembly approaches a PUT edge because the field tends to distort around PUT edges causing the test probe to saturate and miss a surface flaw or anomaly located near the PUT edge.

16 Claims, 2 Drawing Sheets

6,114,849

FLEXIBLE EDDY CURRENT TEST PROBE

FIELD OF THE INVENTION

This invention relates to non-destructive inspection and testing of electrically conductive parts. More particularly, this invention relates to an eddy current test probe having a flexible sensor assembly for detecting near surface flaws or anomalies in the material structure of conductive parts.

BACKGROUND OF THE INVENTION

Using eddy current test systems for non-destructive testing of parts formed of conductive materials is common in a variety of environments. The testing applications include but are not limited to alloy sorting, detecting cracks in air frames and engines, and remotely testing structures in hazardous environments, such as tubing in nuclear power plant heat exchanger units. Such testing applications are frequently essential for controlling the quality of the manufactured part and preventing potentially catastrophic failures of structural members, weldments, and other joints.

Typically, an eddy current test system consists of an eddy current probe coupled to a display. The display provides a visual read out of the eddy current signal strength generated in the conductive part. The eddy current signal strength varies depending on near surface defects or flaws detected in the material of the conductive part.

The eddy current test system provides an alternating voltage to a drive coil which is part of the eddy current probe. The drive coil is brought into contact with the Part Under Test ("PUT") made of a conductive material. The alternating voltage present in the drive coil induces an electromagnetic field in the PUT. The electromagnetic field, in turn, generates eddy currents in the conductive part. Thus, eddy currents exist as a result of voltages induced in the body of the conductive PUT by variations of the magnetic flux. The variation of the magnetic flux is the result of a varying magnetic field or of the relative motion of the conductive part with respect to the magnetic field.

A receive coil is typically positioned in close proximity to the drive coil. The receive coil receives the eddy currents and sends the signals to the test system display for displaying the eddy current signal strength in suitable units. A near surface flaw or anomaly in the conductive part changes the electromagnetic field and consequently, the eddy current signal strength, received by the receive coil. Although the change in the electromagnetic field in the conductive part is commonly weak and difficult to repeatably measure, the change in the eddy current signal strength is much more dramatic and easily and repeatably measurable.

There are several problems associated with known eddy current test systems. An important requirement in eddy current testing is that the drive and/or receive coil remain in close contact with the PUT to maximize the electromagnetic field induced in the PUT. Often, the drive coil and/or the receive coil lifts off the PUT as the eddy current test probe traverses the PUT. If either coil lifts off the PUT, the electromagnetic field injected into the part is dramatically weakened, reducing the eddy current signal strength received by the receive coil. This reduction in the received eddy current signal strength can falsely signal a defect or anomaly in the PUT.

Moreover, traditional eddy current test systems include sensor assemblies having fixed-shaped drive and receive coils. Fixed-shaped coils do not maximize surface contact with the PUT because they do not flex to accommodate differently shaped PUTs. Attempts to maximize surface contact with the PUT have produced multiple coil arrays. U.S. Pat. No. 5,389,876, to Hedengren et al., issued Feb. 14, 1995, describes a multiple coil array eddy current test system. The multiple coil array described in Hedengren provides a degree of coil flexibility not found in fixed-coil assemblies. However, the Hedengren test system requires a spatially correlated coil array of substantially identical probe elements which, in turn, necessitates tightly controlled and complex manufacturing processes. Moreover, multiple coil arrays such as the coil array described in Hedengren require stringent and involved electrical connections.

Accordingly, a need remains for an eddy current test probe having a sensor assembly which is flexible, maximizes surface contact with the PUT, prevents coil lift off, is easy to manufacture, and simplifies the required electrical connections. A need also remains for an eddy current test probe that is repeatable, accurate, reliable, and easy to use.

SUMMARY OF THE INVENTION

The present invention relates to an eddy current test probe having a flexible sensor assembly for non-destructive testing of conductive parts. The flexible eddy current sensor assembly includes a coil assembly having a drive coil and a receive coil. The drive coil receives an alternating voltage from an external alternating voltage source. The receive coil and the drive coil are positioned in close proximity to each other. The receive coil receives the eddy currents induced in the PUT. The receive coil is coupled to a visual display which displays the eddy current signal strength in appropriate units. The coil assembly is formed around a flexible membrane. The flexible membrane allows the coil assembly to contour to the PUT surface. By doing so, surface coupling is not only maintained but maximized between the PUT and the coil assembly which, in turn, improves the induced eddy currents and the accuracy of the testing.

A wear resistant film wraps around the outside of the flexible membrane enclosing the coil assembly. The wear resistant film prevents damage to the coils from the inevitable surface irregularities and abrasive particles found in PUTs. The flexible membrane is wrapped around a flexible compliance membrane. The compliance membrane provides a degree of stiffness to the flexible membrane for maintaining close surface coupling with the PUT.

An electromagnetic shield optionally wraps around compliance membrane on each side of the coil assembly and underneath the wear resistant film. The electromagnetic shield contains the energy exchange between the PUT and the coil assembly by preventing the electromagnetic field induced in the PUT from spreading out on the PUT. The electromagnetic shield is of particular importance when the sensor assembly approaches a PUT edge because the field tends to distort around PUT edges which can cause the eddy current test system to fail.

The foregoing and other objects, features, and advantages of the invention will become more readily apparent from the following detailed description of a preferred embodiment which proceeds with reference to the drawings.

DETAILED DESCRIPTION OF THE PREFERRED EMBODIMENT

Figure 1A:
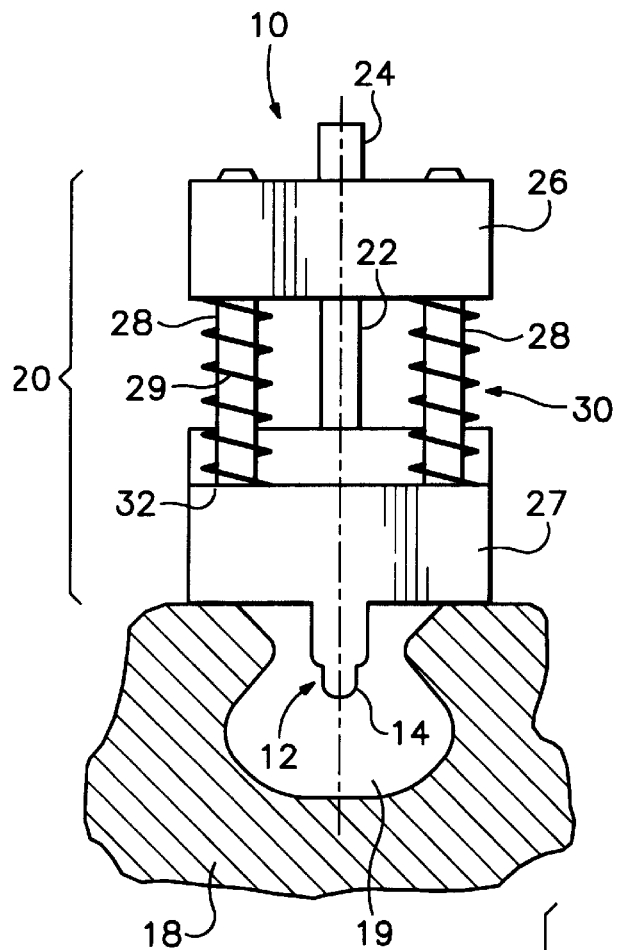
FIG. 1A is an end view of an eddy current test system according to the present invention where the flexible sensor assembly is retracted.
Figure 1B:
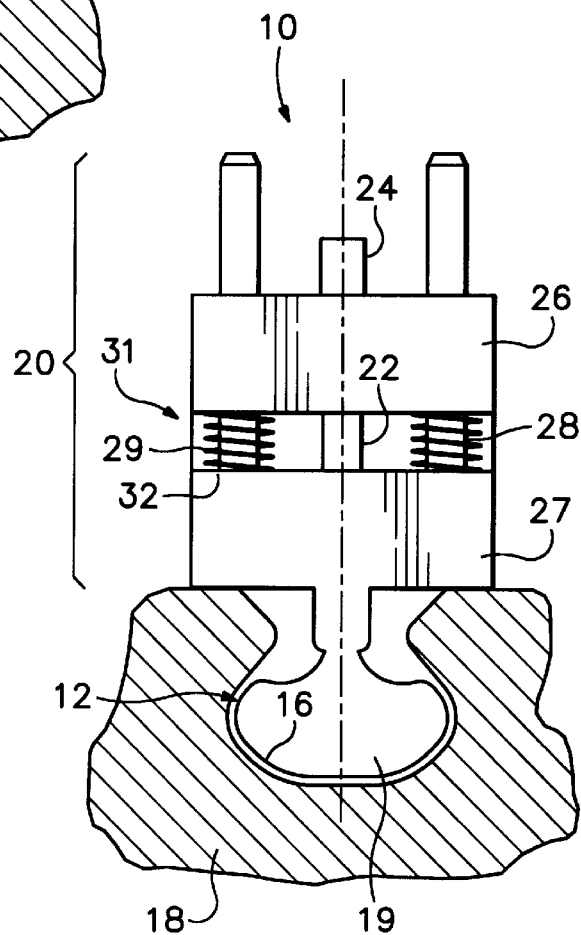
FIG. 1B is an end view of an eddy current test system according to the present invention where the flexible sensor assembly is extended.

Referring to FIGS. 1A and 1B, the flexible eddy current test probe 10 includes a sensor fixture 20 and a flexible sensor assembly 12. The sensor fixture 20 positions the sensor assembly 12 over the PUT 18 when the sensor assembly 12 is in the retracted position 14 shown in FIG. 1A. Once positioned, the sensor assembly fixture 20 projects the sensor assembly 12 out into the extended position 16 shown in FIG. 1B. By doing so, the flexible sensor assembly 12 contours around the PUT slot or crevice 19 thereby improving the surface coupling between the sensor assembly 12 and the PUT 18.

Figure 2:
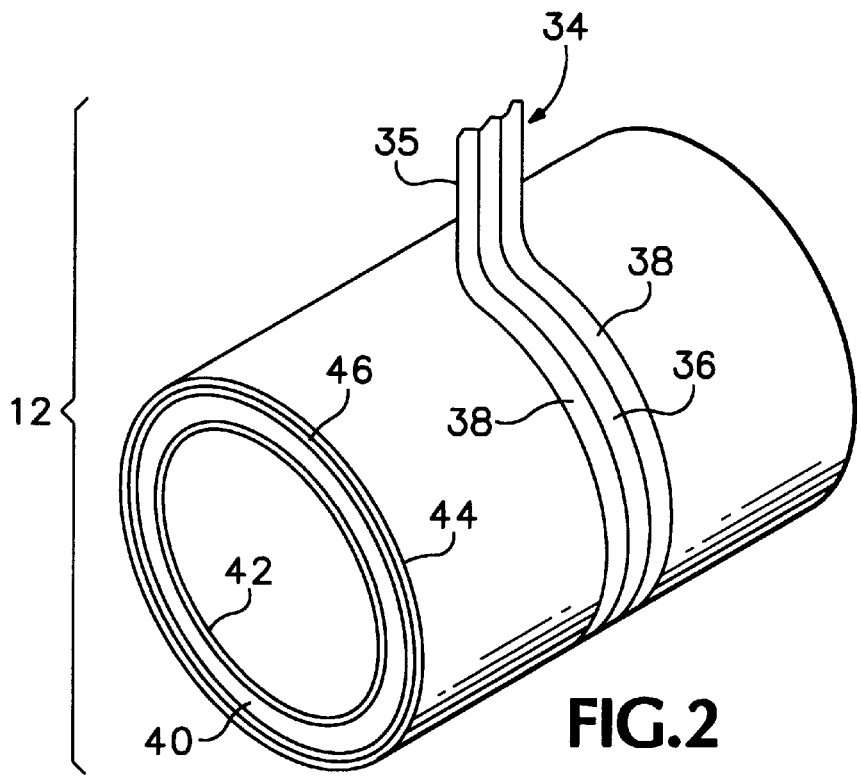
FIG. 2 is an end view of the flexible sensor assembly shown in FIGS. 1A and 1B.
Figure 3:
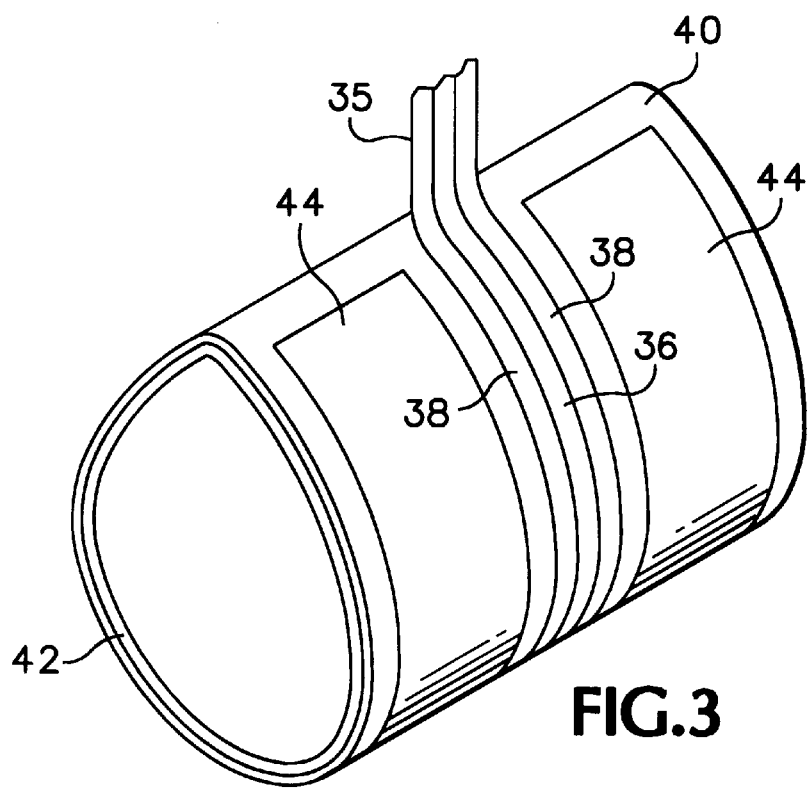
FIG. 3 is a side view of the flexible sensor assembly shown in FIGS. 1A and 1B.

The sensor assembly fixture 20 can have a variety of shapes and dimensions depending on many factors, including the shape of the PUT 18, the type of sensor assembly 12, the testing application, and whether the test will be conducted by hand or machine. FIGS. 1A and 1B illustrates one embodiment of the sensor fixture 20. The fixture 20 includes a central shaft 22, a top portion 26, a bottom portion 27, side shafts 28, springs 29, and a locking mechanism 32 (not shown). The top portion 26 and the bottom portion 27 are substantially vertically aligned. The central shaft 22 extends longitudinally from substantially the center of top portion 26 to substantially the center of bottom portion 27 That is, the central shaft 22 traverses the bottom portion 27 and the top portion 26 at a first and second end, respectively. At the first end, the central shaft 22 is attached to the sensor assembly 12 through the bottom portion 27. At the second end, the central shaft 22 includes an external connector 24. The connector 24 is electrically connected to the sensor assembly 12 via wires (not shown) that run the length of the central shaft 22, and more particularly as explained below, the connector 24 is electrically connected to the drive coil 36 and the receive coil 38 (FIGS. 2 and 3). Thus, the connector 24 provides a means for external components to electrically connect to the sensor assembly 12 (FIGS. 2 and 3). Typically, the connector 24 couples the sensor drive coil 36 to an alternating voltage source (not shown) and the receive coil 38 to an eddy current display or measurement means (not shown) which displays and/or measures the eddy current signal strength induced in the PUT 18.

The fixture 20 is initially positioned over the PUT 18 with the sensor assembly 12 in the retracted position 14 shown in FIG. 1A. At this time, the top portion 26 and the bottom portion 27 are separated by the length of the side shafts 28 and a portion of the sensor assembly 12 is drawn into the bottom portion 27. Side shafts 28 are positioned on either side of the central shaft 22 and are each encircled by springs 29. The present invention is not limited by the number, shape, or location of side shafts 28 or springs 29 which can vary depending on the many factors identified above. When the sensor assembly 12 is in the retracted position 14, the springs 29 are in the extended position 30 shown in FIG. 1A.

Once the fixture 20 is securely positioned over the PUT 18, the top portion 26 is brought into close proximity with the bottom portion 27 by sliding the top portion 26 down towards the bottom portion 26 along the length of the side shafts 28. Sliding or pushing the top portion 26 down results in compressing the springs 29 into the compressed position 31 shown in FIG. 1B. By doing so, the central shaft 22 moves down into the bottom portion 27 causing the portion of the sensor assembly 12 drawn back into the bottom portion 27 to project out from the fixture 20 and change from the retracted positon 14 to the extended position 16. Since the sensor assembly 12 is formed from flexible materials, the sensor assembly 12 in the extended position 16 contours inside the PUT 18 crevice or slot 19 as shown in FIG. 1B. The fixture 20 includes a locking mechanism 32 (not shown) that fixes the sensor assembly 12 in the extended position 16.

FIG. 2 illustrates the construction of the test sensor assembly 12. The arrangement of the drive coil 36 and receive coil 38 shown in FIG. 2 is presented merely to help visualize the disposition of the coil assembly 34 with respect to the other elements comprising sensor assembly 12 in order to understand a more complicated arrangement of drive and receive coils 36 and 38, respectively.

The test sensor assembly 12 includes a coil assembly 34 having a drive coil 36, a receive coil 38, coil leads 35, a flexible membrane 40, a compliance membrane 42, an electromagnetic shield 44, and a wear resistant film 46. The drive coil 36 is preferably made of conductive wire, such as copper wire, formed on the flexible membrane 40. The drive coil 36 is preferably wrapped around the flexible membrane 40. The configuration of drive and receive coils used can vary without departing from the scope of the present invention. The receive coil 38 shown in FIG. 2 is a differential or reflection coil positioned in close proximity to and on either side of the drive coil 36. Another common coil configuration is a differential coil configuration (not shown) where two receive coils also function as drive coils. The coils in a given probe also vary in the winding direction, i.e., the receive coil may be wound in one direction and the drive coil in another to accommodate additive or subtractive response signal sensitivity. The receive coil 38 is also preferably made of conductive wire, such as copper wire, formed on the flexible membrane 40 by, for example, wrapping the copper wire around the flexible membrane 40.

The flexible membrane 40 is made of a material which is flexible enough to contour around the PUT 18 slot or crevice 19 thereby maximizing the surface coupling between the coil assembly 34 and the PUT 18. The flexible membrane 40 is layered on a compliance membrane 42. The compliance membrane 42 is preferably made of a material stiffer than the flexible membrane 40 and provides a degree of stiffness that the flexible membrane 40 may lack. By layering the flexible membrane 40 with the compliance membrane 42, the test probe 10 can traverse the length of the PUT 18 without the coil assembly 34 lifting off the PUT 18 surface. The flexible membrane 40 is preferably made of a flexible non-conductive material such as cellulose triacetate. The material used to form the compliance membrane 42 can vary depending on the testing application. In some testing applications, the degree of compliance needed will be low requiring a more flexible material forming the compliance membrane 42. In other testing applications, a much more stiff compliance membrane 42 will be more suitable. For most applications, however, the compliance membrane 42 is preferably made of a flexible conductive or non-conductive material such as silastic.

The sensor assembly 12 additionally includes a wear resistant film 46 enclosing the coil assembly 34. Before testing begins, the PUT 18 slot or crevice 19 is often cleaned to remove excessive dirt, oil buildup, or other residue that may interfere with proper testing. While the cleaning process removes oil and other like residue, the cleaning process leaves behind rough metal particles and surface irregularities that damage the fragile drive and receive coils 36 and 38, respectively. The wear resistant film 46 protects the coil assembly 34 from damage caused by such particles and irregularities as the test probe traverses the PUT 18. The wear resistant film 46 is preferably made of a non-conductive flexcircuit material having a coating which allows the test probe 10 to easily slide over the PUT slot or crevice 19. The wear resistant film 46 can also be removably attached to the sensor assembly 12 such that it is easily replaceable and serviceable in the field.

The sensor assembly 12 optionally includes an electromagnetic shield 44. The position of the shield 44 relative to the drive and receive coil 34 and 36, respectively, is best shown in FIG. 3. The shield 44 is formed around the flexible membrane 40 on either side of the receive coils 38. The shield 44 does not electrically contact either the receive coils 38 or the drive coils 36. The electromagnetic shield 44 is preferably made of a conductive material such as copper or aluminum. The shield 44 can either be in the form of a sheet as shown in FIG. 3 or wire. The electromagnetic shield 44 prevents the electromagnetic field induced in the PUT 18 from spreading too far into the PUT 18 surface. The electromagnetic shield 44 confines the field without draining its energy because the shield 44 floats electrically above ground potential. The electromagnetic shield 44 is particularly important when the test probe 10 is brought into close proximity with a PUT 18 edge (not shown). If the electromagnetic field is allowed to spread into the PUT 18, the field becomes distorted before the receive coil 38 measures the eddy currents produced at the PUT 18 edge. Thus, a near surface flaw occurring near the edge of the PUT 18 might not be detected by the test probe 10. Additionally, the distortion of the field near the edge is so much greater than the eddy current signals generally detected by the receive coil 38 causing the instrumentation amplifiers (not shown) receiving the signals measured by the receive coil 38 to saturate. The drive coil 36, the receive coil 38, and the electromagnetic shield 44 can be simultaneously formed using commonly-known photolithography methods.

The test probe 10 operates as follows. The test probe 10 is positioned over the PUT 18 with the sensor assembly 12 in the retracted position 14 shown in FIG. 1A. The sensor fixture 20 then projects the sensor assembly 12 out to the extended position 16 shown in FIG. 1B. The flexible sensor assembly 12 contours to the PUT 18 slot or crevice 19. Once the sensor assembly 12 is brought into close contact with the PUT 18, testing is ready to begin. The drive coil 36 receives an alternating voltage from an external alternating voltage source (not shown) electrically connected to the drive coil 36 via the connector 24. The alternating voltage applied to the drive coil 36 induces an electromagnetic field in the PUT 18. The time variations of the electromagnetic field in the PUT 18 generates eddy currents.

The receive coil 38 is positioned in close proximity to the drive coil 36 to maximize inductive coupling through the inspection surface of the PUT 18. The receive coil 38 detects the induced eddy currents and sends the information to the external display and measurement device (not shown) via connector 24. The display and measurement device displays and measures the eddy current signal strength in suitable units on the test system display (not shown) as the test probe 10 is traversed over the PUT 18. A near surface flaw or an anomaly in the PUT 18 changes the electromagnetic field and consequently, in the eddy current signal strength, received by the receive coil 38. Although the change in the electromagnetic field in the conductive part is commonly weak and difficult to repeatably measure, the change in the eddy current strength is much more dramatic and easily and repeatably measurable.

Having illustrated and described the principles of the invention in a preferred embodiment thereof, it should be readily apparent to those skilled in the art that the invention can be modified in arrangement and detail without departing from such principles. We claim all modifications coming within the spirit and scope of the following claims.

We claim:

1. A flexible eddy current sensor assembly for detecting flaws and anomalies in a conductive part, comprising:
   a first flexible membrane;
   a drive coil formed on a first side of the first flexible membrane for inducing a magnetic field in the conductive part;
   a receive coil formed on the first side of the first flexible membrane for sensing eddy currents produced by the magnetic field induced in the conductive part; and
   a second flexible membrane layered on a second side of the first membrane, the second membrane being stiffer than the first membrane;
   wherein the first and second flexible membranes adaptively contour to the conductive part.

2. The flexible eddy current sensor assembly of claim 1 wherein the first flexible membrane is formed of a substantially non-conductive material and the second flexible membrane is formed of either a substantially non-conductive or a substantially conductive material.

3. The flexible eddy current sensor assembly of claim 1 wherein the first flexible membrane is formed of a cellulose triacetate material and the second flexible membrane is formed of a silastic material.

4. The flexible eddy current sensor assembly of claim 1 wherein the drive coil and the receive coil are wound around the first flexible membrane.

5. The flexible eddy current sensor assembly of claim 1 further including an electromagnetic shield formed on the first side of the first flexible membrane adjacent to the receive coil for containing the electromagnetic field induced in the conductive part.

6. The flexible eddy current sensor assembly of claim 5 wherein the electromagnetic shield is made of copper.

7. The flexible eddy current sensor assembly of claim 1 further including a wear resistant film formed over the drive and receive coil.

8. An eddy current test probe for non-destructive testing of a conductive part, comprising:
   a sensor assembly having an extended and a retracted position, the sensor assembly adaptively contouring to a part under test when in the extended position, the sensor assembly including:
   a first flexible membrane for adaptively contouring to the surface of the part;
   a drive coil formed on the flexible membrane for inducing a magnetic field in the part under test;
   a receive coil formed on the flexible membrane and positioned in close proximity to the drive coil for sensing eddy currents produced by the induced magnetic field in the part under test; and
   a second flexible membrane layered to the first flexible membrane for adaptively contouring to the surface of the part, the second membrane being stiffer than the first membrane; and
   a holder attached to the sensor assembly for retracting or extending the sensor assembly.

9. The eddy current test probe of claim 8 including a supporting liner formed of a first flexible material inside the flexible membrane and wherein the flexible membrane is formed of a second flexible material, the first flexible material being stiffer than the second flexible material.

10. The eddy current test probe of claim 8 wherein the sensor assembly includes an electromagnetic shield formed over the first flexible membrane for containing the electromagnetic field induced in the part.

11. The eddy current test probe of claim 10 wherein the electromagnetic shield is formed of copper.

12. The eddy current test probe of claim 8 wherein the sensor assembly includes a wear resistant membrane enclosing the drive and receive coils for preventing wear to the drive and receive coils.

13. A method for non-destructively determining the presence of surface flaws in an electrically conductive object by means of an eddy current test probe having a holder and a flexible sensor assembly, the sensor assembly including a flexible drive coil and a flexible receive coil formed on a flexible membrane, the method comprising:

positioning the eddy current test probe over the object with the sensor assembly in a retracted position;

extending the sensor assembly so that the flexible membrane conforms to contours of the object thereby inducing surface coupling between the drive and receive coils and the object;

inducing eddy currents into the object by providing an alternating voltage to the drive coil; and sensing the induced eddy currents in the receive coil as the test probe traverses the object.

14. The method of claim 13 wherein the flexible sensor assembly includes a second flexible membrane, the flexible membrane superimposed on the second flexible membrane, the method including forming the second flexible membrane of a material stiffer than a material forming the flexible membrane.

15. The method of claim 13 further including enclosing the drive and receive coil in a wear resistant film for preventing damage to the drive and receive coils.

16. The method of claim 13 wherein the flexible sensor assembly includes an electromagnetic shield superimposed over the flexible membrane and in close proximity to the drive and receive coils, the method including inducing an electromagnetic field in the object and preventing the induced electromagnetic field from emanating beyond the edges of the electromagnetic shield by trapping the field in the electromagnetic shield.

* * * * *

UNITED STATES PATENT AND TRADEMARK OFFICE
CERTIFICATE OF CORRECTION

PATENT NO.   : 6,114,849
DATED        : September 5, 2000
INVENTOR(S)  : Price et al.

It is certified that error appears in the above-identified patent and that said Letters Patent is hereby corrected as shown below:

Column 3,
Line 64, "bottom portion 26" should read -- bottom portion 27 --

Signed and Sealed this

Thirtieth Day of April, 2002

Attest:

Attesting Officer

JAMES E. ROGAN
*Director of the United States Patent and Trademark Office*